CHRYSANTHEMUM PLANT
Filed Jan. 17, 1972 2 Sheets-Sheet 1
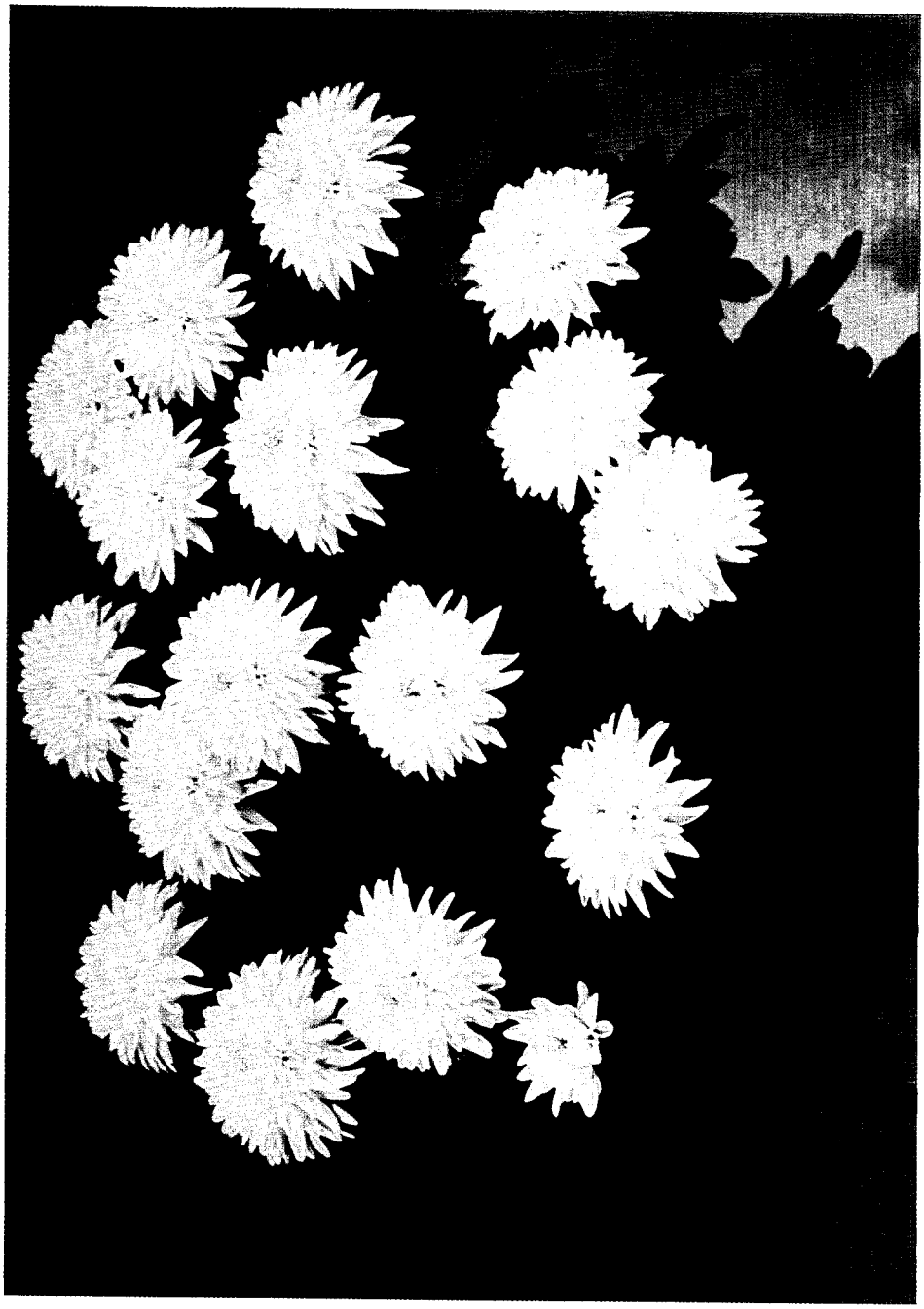

CHRYSANTHEMUM PLANT
Filed Jan. 17, 1972 2 Sheets-Sheet 2
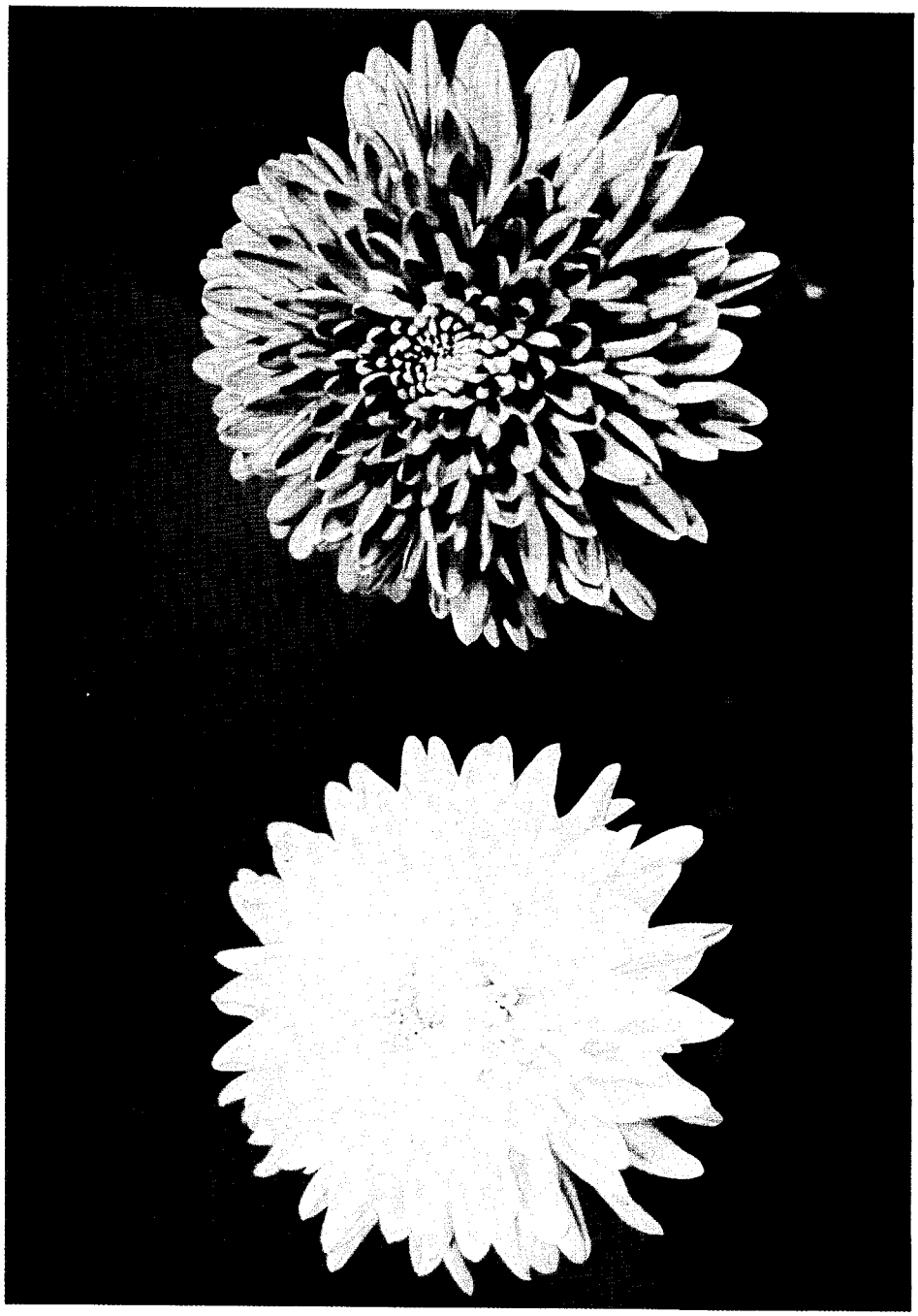

United States Patent Office

Plant Pat. 3,421

Patented Jan. 1, 1974

3,421
CHRYSANTHEMUM PLANT

Jack S. Sweet, St. Petersburg, Fla., and Walter H. Jessel, Jr., Doylestown, and William E. Duffett, Akron, Ohio, assignors to Earl J. Small Growers Inc., Pinellas Park, Fla.

Filed Jan. 17, 1972, Ser. No. 218,568
Int. Cl. A01h *5/00*
U.S. Cl. Plt.—78 1 Claim

The present invention comprises a new and distinct cultivar of chrysanthemum plant which is a sport of the unpatented cultivar known commercially in the United States as Torch.

The new cultivar is similar in many respects to Torch, having the same characteristics of:

(1) Decorative flower form.
(2) Foliage shape and color.
(3) Flowering response.

The new cultivar is distinguished from Torch by the following characteristics when grown under comparable conditions:

(1) Its yellow color when bud development and finishing temperatures are above 65°–70° F. Below this temperature level it flowers yellow with bronze tinging.
(2) Flowers approximately one-half inch smaller.
(3) Approximately 1″ shorter habit.
(4) Foilage approximately one-half inch shorter in length.

The new cultivar was discovered at Pinellas Park, Fla. in the form of a plant with a yellow sectorial flower on one of the breaks, and when asexually reproduced by cuttings at Barberton, Ohio was successfully recovered and found to retain its distinctive characteristics through successive propagations.

The new cultivar when grown in the vicinity of Barberton, Ohio, has a response period of approximately 9–10 weeks, and the following detailed description is based on observations made of the new cultivar in a greenhouse in Barberton, Ohio. The response time, blooming period, color and total vigor may vary significantly with varying environmental conditions such as temperature, day length, and light intensity. Suggested flowering in the northern and western United States is from July through mid-November; south and southwest, May through November.

The accompanying photographic drawings show the unique characteristics of our new cultivar, the color being as nearly true as possible with color illustrations of this type. Sheet one of the drawings is a photograph of the new cultivar by itself, and sheet two comprises a comparison photograph, with the new cultivar appearing on the left and the parent cultivar Torch on the right.

In the following description, color references are made to the Munsell Color Book, 1963 edition, and comparisons are made with the parent cultivar Torch. Where only a single value or description appears for the new cultivar, the same value or description applies as well to the parent cultivar. It should further be noted that the color designations for the new cultivar are where both bud development and finishing temperatures are above 65°–70° F. At temperatures below this range, bronze tinging will appear in the new cultivar.

Botanical classification: *Chrysanthemum morifolium*

| | Yellow Torch | Torch |
|---|---|---|
| **Bloom:** | | |
| Size | 3″ | 3″–3½″. |
| Fully expanded | 3½″ | 4″. |
| Borne | Singly on disbudded stems | |
| Stems | Strong | |
| Form | Decorative | |
| Permanence | 14–16 days | |
| **Color:** | | |
| Center of flower | Yellow green, 10Y8.5/10 | Approximately bronze, 10R4/10. |
| Base of petals | do | Do. |
| Inside of petals | Dark yellow, 6.25Y8.5/12 to light yellow, 7.5Y9/6 | Approximately bronze, 10R4/10 to light bronze, 5YR/5 10. |
| Reverse of petals | Light yellow, 7.5Y9/6 | Approximately light bronze, 10YR7/6. |
| Tonality from a distance | Yellow | Bronze. |
| Discoloration | Light yellow, 7.5Y9/6 | Approximately light bronze, 5YR5/10. |
| **Petals:** | | |
| Texture | Smooth | |
| Appearance and form | Tubular at base, open quickly to a two-ridged shallow keel, tapering to a two-notched point. | |
| Arrangement | Composite, whorled on a single receptacle | |
| Persistence | Resist shatter | |
| Fragrance | Typical chrysanthemum | |
| **Reproductive organs:** | | |
| Stamen, anthers | None–10 | |
| Pollen | None to very scant | |
| Arrangement | Clustered in center of flower, if present | |
| Styles | Present both ray and disc florets | |
| Length | Short | |
| Ovaries | At the base of petal attached to receptacle | |
| **Plant:** | | |
| Form | Herbaceous | |
| Growth | Upright | |
| Height | Approximately 10″–14″ given 9 week short treatment timing for the various seasons, as defined in the timetables of Yoder Brothers, Inc., Barberton, Ohio. | Approximately 11″–15″ given 9 week short treatment timing for the various seasons, as defined in the timetables of Yoder Brothers, Inc., Barberton, Ohio. |
| Spread | Approximately 4¾″ as a pinched plant when given 9 week short treatment timing for the various seasons, as defined in the Yoder timetables. | Approximately 5″ as a pinched plant when given 9 week short treatment timing for the various seasons, as defined in the Yoder timetables. |
| **Foliage:** | | |
| Top side | Very dark green, 10GY2/4 | |
| Size | 4″ long, 2″ wide | 4½″ long, 2¾″ wide. |
| Quantity | Numerous | |
| Shape | Spatulate lobed | |
| Texture | Smooth | |
| Ribs and veins | Prominent | |
| Edge | Moderately indented | |
| Serration | Moderate | |
| Under side | Medium green, 7.5GY4/4 | |
| Stipules | Very prominent | Rudimentary. |

We claim:

1. A new and distinct cultivar of chrysanthemum characterized particularly as to its uniqueness when compared to the parent cultivar Torch by its yellow flower color when bud development and finishing temperatures are above 65°–70° F., flowers which are approximately one-half inch smaller, approximately 1″ shorter habit, and by its foliage which is approximately one-half inch shorter in length.

No references cited.

ROBERT E. BAGWILL, Primary Examiner.

UNITED STATES PATENT OFFICE
CERTIFICATE OF CORRECTION

Patent No. PP-3,421 Dated January 1, 1974

Inventor(s) JACK S. SWEET, WALTER H. JESSEL, JR. and WILLIAM E. DUFFETT

It is certified that error appears in the above-identified patent and that said Letters Patent are hereby corrected as shown below:

In the tabulated description below Columns 1 and 2, under "Color:" opposite "Inside of petals" and in the column for "Torch", the description should read "...to light bronze, 5YR5/10".

Signed and sealed this 1st day of October 1974.

(SEAL)
Attest:

McCOY M. GIBSON JR.
Attesting Officer

C. MARSHALL DANN
Commissioner of Patents

USCOMM-DC 60376-P69
U.S. GOVERNMENT PRINTING OFFICE 1969 O—366-334